United States Patent
Berzak et al.

(10) Patent No.: US 8,709,005 B2
(45) Date of Patent: Apr. 29, 2014

(54) COILED HEAT EXCHANGER FOR CRYOSURGICAL INSTRUMENT

(75) Inventors: Nir Berzak, Givataim (IL); Ron Hilleli, Zichron Yaacov (IL)

(73) Assignee: IceCure Medical Ltd., Caesarea (IL)

( * ) Notice: Subject to any disclaimer, the term of this patent is extended or adjusted under 35 U.S.C. 154(b) by 213 days.

(21) Appl. No.: 13/232,203

(22) Filed: Sep. 14, 2011

(65) Prior Publication Data

US 2012/0289953 A1 Nov. 15, 2012

Related U.S. Application Data

(60) Provisional application No. 61/484,822, filed on May 11, 2011.

(51) Int. Cl.
*A61B 18/02* (2006.01)
(52) U.S. Cl.
USPC .......................................................... 606/23
(58) Field of Classification Search
USPC .................................................... 606/20–26
See application file for complete search history.

(56) References Cited

U.S. PATENT DOCUMENTS

| | | | |
|---|---|---|---|
| 3,800,552 A * | 4/1974 | Sollami et al. .................. | 62/293 |
| 5,800,487 A * | 9/1998 | Mikus et al. .................. | 607/105 |
| 6,929,639 B2 * | 8/2005 | Lafontaine ...................... | 606/20 |
| 2005/0043725 A1 * | 2/2005 | Duong et al. .................... | 606/23 |
| 2006/0079867 A1 | 4/2006 | Berzak et al. | |

FOREIGN PATENT DOCUMENTS

WO  WO 2009/128014  10/2009

OTHER PUBLICATIONS

International Search Report and Written Opinion of the International Searching Authority received in co-pending PCT Application No. PCT/US2011/051529.

* cited by examiner

*Primary Examiner* — Michael Peffley
*Assistant Examiner* — Daniel Fowler
(74) *Attorney, Agent, or Firm* — The Law Office of Michael E. Kondoudis

(57) ABSTRACT

A cryosurgical instrument including: a shaft having a closed distal end defining an expansion chamber and an open proximal end adapted and configured to receive an inflow of cryogen and to exhaust a flow of expanded cryogen; and a heat exchanger. The heat exchanger includes: a plurality of cryogen delivery tubes that spiral around a longitudinal axis thereof; and a diffuser having a plurality of branches, each of the branches supplying received cryogen to a respective one of the delivery tubes. The cryogen delivery tubes, where they spiral, are spaced from each other and in fluid tight contact with the inner surface of the shaft so as to form spiraling cryogen exhaust pathways that extend along a portion of a length of the cryosurgical instrument from the distal end of the shaft.

4 Claims, 8 Drawing Sheets

COILED HEAT EXCHANGER FOR CRYOSURGICAL INSTRUMENT

CROSS-REFERENCE TO RELATED APPLICATION

This application claims the benefit of U.S. provisional patent application No. 61/484,822, filed May 11, 2011.

BACKGROUND

1. Technical Field

Embodiments of the present invention relate generally to cryosurgical instruments such as cryoprobes and, more particularly, to cryosurgical instruments featuring a coiled tube heat exchanger.

2. Description of Related Art

It is known to employ coiled heat exchangers in cryosurgical instruments with cryogen supplied as a pressurized gas. In such heat exchangers, the expansion of the gas causes it to change its temperature. As explained in U.S. Pat. No. 6,706,037, for example, this phenomenon is referred to as the "Joule-Thomson effect", thermodynamically known as adiabatic expansion.

It is also known, in coiled heat exchangers, to use gases that cool upon expansion, such as Argon or Nitrogen, for cooling, and gases that heat as a result of the expansion, such as Helium, for heating. In these heat exchangers, the return gases are commonly used to recycle the thermal energy (i.e., the return cooling gas not only cools the outer surface of the cryosurgical instrument but also the inlet pressurized gas). See, for example, U.S. Pat. No. 6,706,037 (at column 15 lines 40-58, and column 16 lines 65-68). Also, as discussed in U.S. Pat. Nos. 3,800,552 and 5,522,870, lowering the inlet temperature may liquefy the expanded gas.

Still further, approaches to enhancing the cooling and heating regeneration are known. For example, U.S. Pat. No. 5,800,487 discusses enhancing the cooling and heating regeneration by supplying the inlet pressurized gas tube with fins to increase the area of the heat exchanging.

If the cryogen is supplied as a liquid or a two-phase (gas/liquid) fluid, cooling methods use the energy required for the change of phase of the inlet cryogen. In this case, the temperature of the inlet fluid and the return fluid may be the same or close in value, and would minimize, or annul heat exchange between the inlet and outlet fluids, due to a small differential temperature. The application of coil serves as a separator of the phases in a two-phase flow. This is because the liquid phase has greater specific gravity, which causes the liquid phase to the outer (greater) diameter. The greater diameter of the coil is close to the external surface and, as a result, the boiling or change of phase of the liquid occurs close to the external surface.

When the cryogens, either in gaseous form or two-phase form, enter in a straight inlet tube, or lumen, flow directing elements (such as those described in U.S. Pat. No. 5,800,487) or baffles (such as those described in U.S. Patent Publication No. 2009/0163902 A1, U.S. Patent Publication No. 2007/0149957 A1, U.S. Patent Publication No. 2007/0149959 A1, and U.S. Patent Publication No. 2009/0182320 A1) have been used.

BRIEF SUMMARY

In one aspect, the innovation disclosed herein yields increased performance of a cryosurgical device by selectively locating the boiling of cryogen in the device. In one implementation, a cryosurgical instrument comprises a coiled tube heat exchanger in which a fluid cryogen flows into a coil that is in energy exchange contact with the outer wall of a portion of a cryosurgical instrument. The heat exchange zone comprises at least the distal/downstream tip of the cryosurgical instrument.

One aspect of the present application provides a cryosurgical instrument including: a shaft having a closed distal end defining an expansion chamber and an open proximal end adapted and configured to receive an inflow of cryogen and to exhaust a flow of expanded cryogen; and a heat exchanger. The heat exchanger includes: a plurality of cryogen delivery tubes that spiral around a longitudinal axis thereof; and a diffuser having a plurality of branches, each of the branches supplying received cryogen to a respective one of the delivery tubes. The cryogen delivery tubes, where they spiral, are spaced from each other and in fluid tight contact with the inner surface of the shaft so as to form spiraling cryogen exhaust pathways that extend along a portion of a length of the cryosurgical instrument from the distal end of the shaft.

Another aspect of the present invention provides a cryosurgical instrument including: a shaft having a closed distal end defining an expansion chamber and an open proximal end adapted and configured to receive an inflow of cryogen and to exhaust a flow of expanded cryogen; and a heat exchanger. The heat exchanger includes: a solid core element extending along a longitudinal axis of the heat exchanger; and a cryogen delivery tube that spirals around and contacts the solid core element. The spirals of the cryogen delivery tube are spaced from each other and in fluid tight contact with the solid core and an inner surface of the shaft so as to form a spiraling cryogen exhaust pathway from the distal end of the shaft to the proximal end of the shaft.

Still another aspect of the present invention provides a cryosurgical instrument including: a shaft having a closed distal end defining an expansion chamber and an open proximal end adapted and configured to receive an inflow of cryogen and to exhaust a flow of expanded cryogen; and a heat exchanger. The heat exchanger includes: a solid core element extending along a longitudinal axis of the heat exchanger; and first and second cryogen delivery tubes, the first cryogen delivery tube including an uncoiled portion extending along the longitudinal axis and a coiled portion that spirals around and contacts the solid core element, the second cryogen delivery tube having a coiled portion that spirals around and contacts the uncoiled portion of the first cryogen delivery tube. The coiled portions are spaced apart. The spirals of the cryogen delivery tubes are spaced from each other and in fluid tight contact with an inner surface of the shaft so as to form a spiraling cryogen exhaust pathway from the distal end of the shaft to the proximal end of the shaft.

Yet another aspect of the present invention provides a cryosurgical instrument including: a shaft having a closed distal end defining a tip and an open proximal end adapted and configured to receive an inflow of cryogen and to exhaust a flow of expanded cryogen; a cryogen flow path from a cryogen supply to the distal end and comprising a cryogen inlet tube in fluid communication with a diffuser that is in fluid communication with a plurality of cryogen delivery tubes that spiral around a longitudinal axis thereof, the diffuser having a plurality of branches, each of the branches supplying received cryogen to a respective one of the delivery tubes; an expansion chamber that receives cryogen from the delivery tubes and permits the received cryogen to expand and cool; and a cryogen exhaust path from the distal end to a cryogen exhaust outlet at the proximal end and comprising spaces between the spirals of the delivery tubes, a return plenum, and a return tube between the cryogen inlet tube and an inner surface of the shaft. The cryogen delivery tubes, where they spiral, are spaced from each other and in fluid tight contact with the inner surface of the shaft so as to form spiraling cryogen exhaust pathways that extend along a portion of a length of the cryosurgical instrument from the distal end of the shaft.

The aforementioned and/or other features, aspects, details, utilities, and advantages of the present invention are: set forth in the detailed description which follows and/or illustrated in the accompanying drawings; possibly inferable from the detailed description and/or illustrated in the accompanying drawings; and/or learnable by practice of the present invention.

This Summary is provided to introduce a selection of concepts in a simplified form that are further described below in the Detailed Description. This Summary is neither intended to identify key features or essential features of the claimed subject matter, nor should it be used to limit the scope of the claimed subject matter. Furthermore, the claimed subject matter is not limited to implementations that solve any disadvantage noted in any part of this application.

BRIEF DESCRIPTION OF THE DRAWINGS

The present invention will be more readily understood from the detailed description of embodiments thereof made in conjunction with the accompanying drawings of which.

DETAILED DESCRIPTION

Figure 1A:
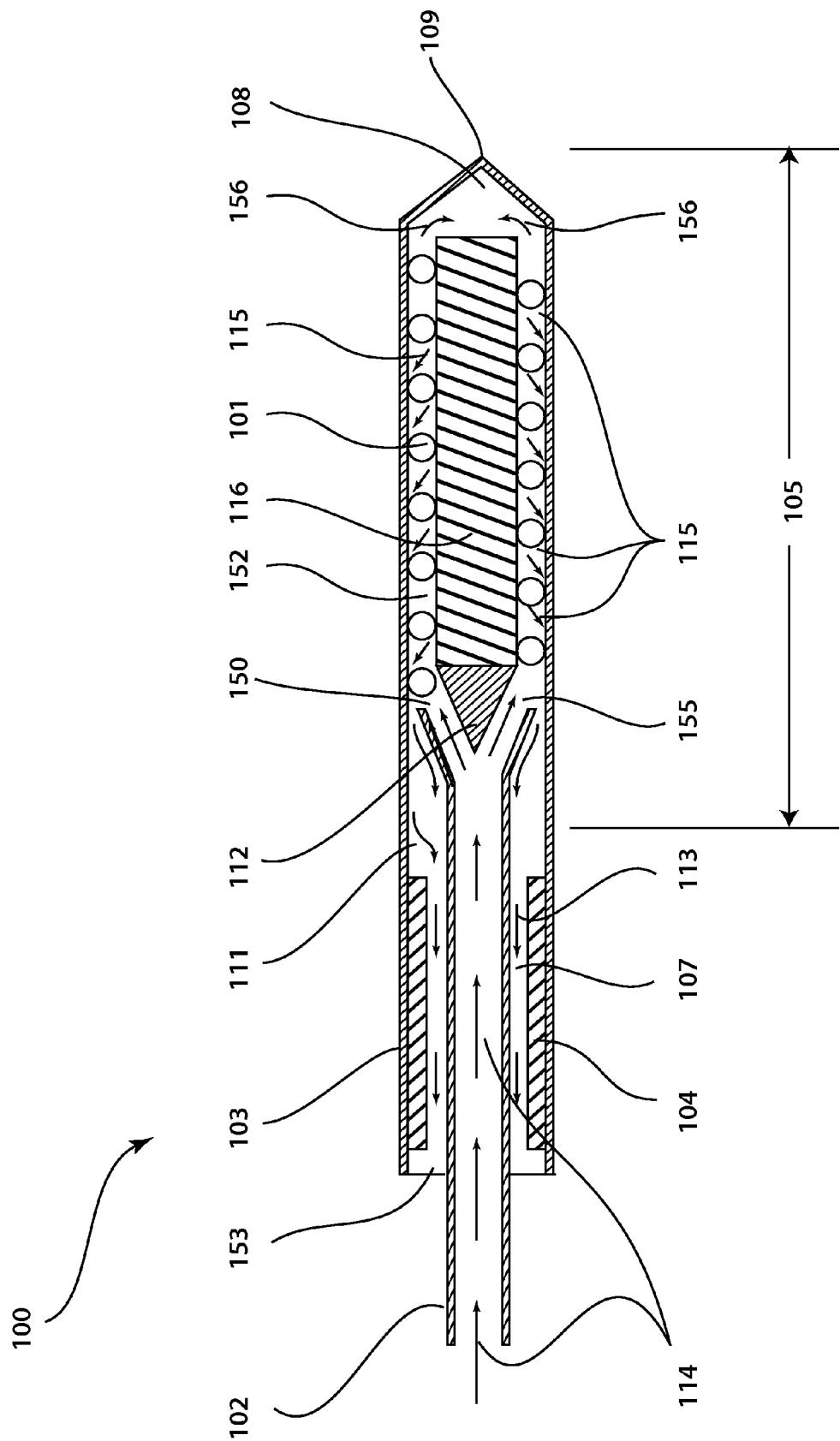
FIGS. 1A and 1B illustrate a non-limiting example of a cryosurgical instrument consistent with an exemplary embodiment of the present invention.

Reference will now be made in detail to embodiments of the present invention, examples of which are illustrated in the accompanying drawings, wherein like reference numerals refer to the like elements throughout. The embodiments are described below to explain the present invention by referring to the figures.

Although the following text sets forth a detailed description of at least one embodiment or implementation, it is to be understood that the legal scope of protection of this application is defined by the words of the claims set forth at the end of this disclosure. The detailed description is to be construed as exemplary only and does not describe every possible embodiment since describing every possible embodiment would be impractical, if not impossible. Numerous alternative embodiments and/or implementations are both contemplated and possible, using either current technology or technology developed after the filing date of this patent, which would still fall within the scope of the claims It is to be understood that, unless a term is expressly defined in this application using the sentence "As used herein, the term " "is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term by limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

Figure 1B:
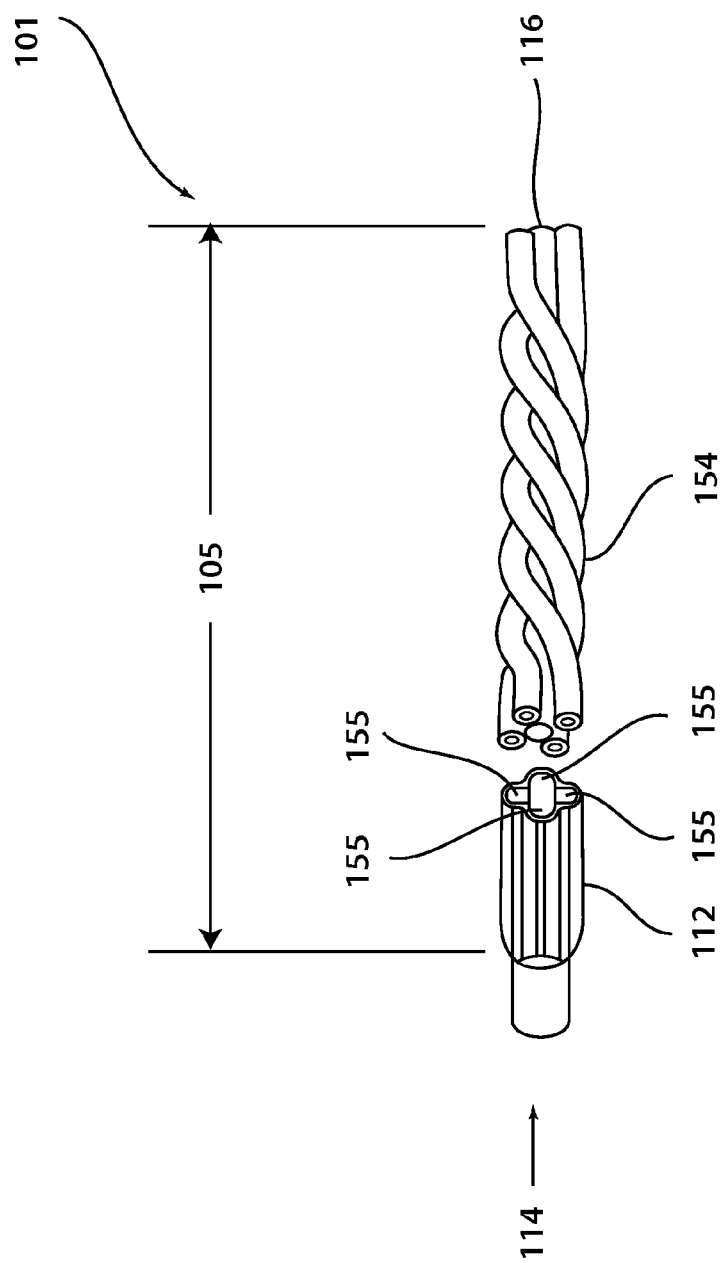

Referring to FIGS. 1A and 1B, there is shown a non-limiting example of a cryosurgical instrument comprising a heat exchanger that features multiple helical coils, which is consistent with an exemplary embodiment of the present invention. FIG. 1A is cross-sectional view of the cryosurgical instrument 100 with the heat exchanger 101. FIG. 1B shows the heat exchanger 101 without the cryosurgical instrument 100.

As shown, the cryosurgical instrument 100 includes a shaft 103 surrounding an inlet 102, a diffuser 112 connected to a core 116, a helical (i.e. coiled) heat exchanger 101, and a tip 109. The portion of the cryosurgical instrument from the tip 109 to just past the diffuser 112 defines a cooling zone 105. Freezing of tissue occurs around the cooling zone 105.

The inlet 102 receives cryogen and delivers the received cryogen into the shaft 103. The shaft 103 features insulation 104 that surrounds the shaft 103 and is mounted to the inner surface of the shaft 103. The insulation 104 is disposed outside of the cooling (heat exchange) zone 105. The presence of the insulation 104 ensures that freezing occurs only where treatment is desired, which is around the cooling zone 105.

In operation, cryogen enters through the inlet 102, as indicated by inlet flow arrows 114, to the diffuser 112. The flow then enters the diffuser 112, which divides the flow into a plurality of branches 155, of which two are shown for the purpose of illustration only. From the branches 155 of the diffuser 112, the flow enters the heat exchanger 101 through an entrance 150 thereof.

The diffuser 112 preferably comprises four branches 155 as shown in FIG. 1B. However, it is to be understood that other numbers of branches are both contemplated and possible. When formed with four branches, the heat exchanger may comprise four coiled tubes 154, as illustrated in FIG. 1B.

The heat exchanger 101 spirals around the core 116 and between the core and the inner surface of the shaft 103. The flow of cryogen through the coiled tubes 154 of the heat exchanger 101 is subjected to centrifugal forces as previously described, such that cryogen is forced against the outer surface of the heat exchanger 101, which is closest to the inner surface of shaft 103, within the cooling zone 105.

As used herein, the term centrifugal force refers to the tendency of a flow following a curved path to be urged away from the center of curvature due to inertia. Centrifugal force is referred to as a force for convenience and ease of explanation. This centrifugal force urges the liquid phase of two-phase flow following a curved path to be urged away from the center of curvature due to greater specific gravity than the gaseous phase.

As cryogen exits the heat exchanger 101 as indicated by arrows 156, it is reflected against a reflective surface 108 of the tip 109. In this embodiment, the tip 109 is hollow, and the reflective surface 108 is optionally placed close to the inner surface of tip 109 as shown. It is to be understood, however, that the tip 109 need not be hollow and/or the reflective surface 108 may be placed distal to the inner surface of the tip 109 (not shown). Boiling of cryogen occurs within the heat exchanger 101, at reflective surface 108, and in a return flow gap 152 between the coiled tubes 154 of the heat exchanger 101, the core 116, and the inner surface of the outer shaft 103.

After being reflected by the reflective surface 108, the exhausted cryogen flows through the gap 152 between the heat exchanger 101 and the shaft 103, as shown. The curved gap 152 enhances the continued boiling of the liquid phase close to the external wall, as described before. The direction of this return flow is shown by return flow arrows 115. The cryosurgical instrument 100 may optionally include a solid core 116 at the innermost part of the shaft 103 and in cooling zone 105, such that neither the heat exchanger 101 nor the gap 152 are present within the core 116. Instead, both the heat exchanger 101 and the gap 152 are preferably arranged around the core 116 as shown. However, as previously described, heat exchange between the inlet and the outlet flow is negligible in this arrangement, due to the negligible temperature difference between the respective flows.

The return flow of exhausted cryogen leaves the cooling zone 105 and then continues as the return flow 113, as shown, through a return plenum 111 and into a return curved gap 107. The exhausted cryogen then exits through a cryogen exhaust outlet 153 at an end of the cryosurgical instrument 100 distal from the tip 109.

FIG. 1B shows the heat exchanger 101 of FIG. 1A in more detail. As shown in FIG. 1A, the heat exchanger 101 and the diffuser 112 are both disposed in the cooling zone 105. The illustrated heat exchanger 101 includes four coiled tubes 154 arranged around and spiraling (wrapping) around a solid core 116. Each of the four branches 155 of the diffuser 112 feeds into a respective one of the coiled tubes of heat exchanger 101 (i.e., in a 1:1 relationship). The coiled tubes 154 have a spiral shape (and may be said to spiral) and are coiled as shown. This configuration advantageously induces the cryogen flowing through the tubes 154 to undergo centrifugal forces as previously described.

It is to be appreciated that the number of coiled tubes and branches need not be four and that other numbers are both possible and contemplated. It is also to be appreciated that the coiled tubes 154 may spiral at varied spiral pitches.

The return flow is preferably permitted only between the inlet tube of the heat exchanger 101 and the inner surface of the shaft 103 at the cooling zone 105, by providing a core 116 that prevents the return flow from returning through the inner gap of the cryosurgical instrument 100 (i.e., the inlet and the return flow are centrifugal). Flow in the center of the helical coil (defined by coiled tubes 154) would have been straight.

Figure 2:
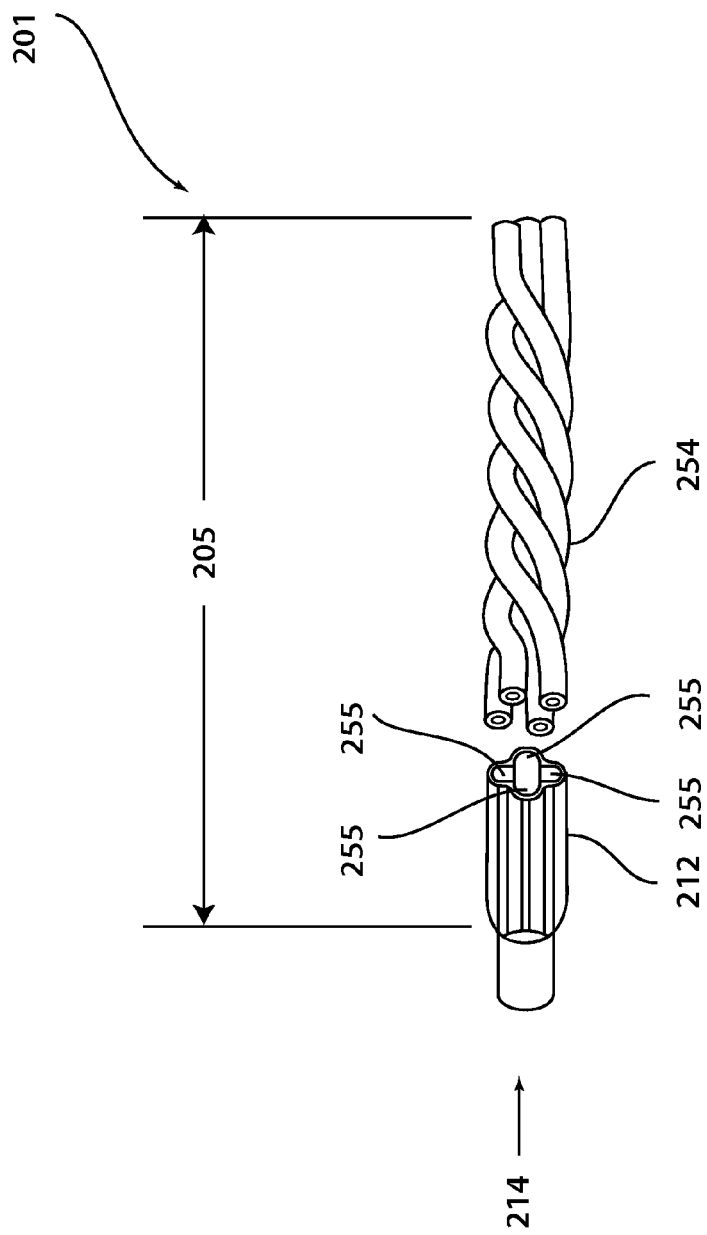
FIG. 2 is a view of a non-limiting example of a heat exchanger consistent with an exemplary embodiment of the present invention.

FIG. 2 shows another non-limiting example of a heat exchanger consistent with an exemplary embodiment of the present invention. The illustrated heat exchanger 201 includes four coiled tubes 254 arranged around and spiraling around a central, longitudinal axis (not shown) in a cooling zone 205 of a cryosurgical device. In contrast to heat exchanger 101 of FIGS. 1A and 1B, heat exchanger 201 does not spiral (i.e., wrap) around a core.

Each of the four branches of the diffuser 212 feeds into a respective one of the coiled tubes of heat exchanger 201 (i.e., in a 1:1 relationship). The coiled tubes 254 spiral and are coiled as shown. This configuration advantageously induces the cryogen flowing through the tubes 254 to undergo centrifugal forces as previously described.

It is to be appreciated that the number of coiled tubes 254 and branches need not be four and that other numbers are both possible and contemplated. It is also to be appreciated that the coiled tubes 254 may spiral at varied spiral pitches.

Figure 3:
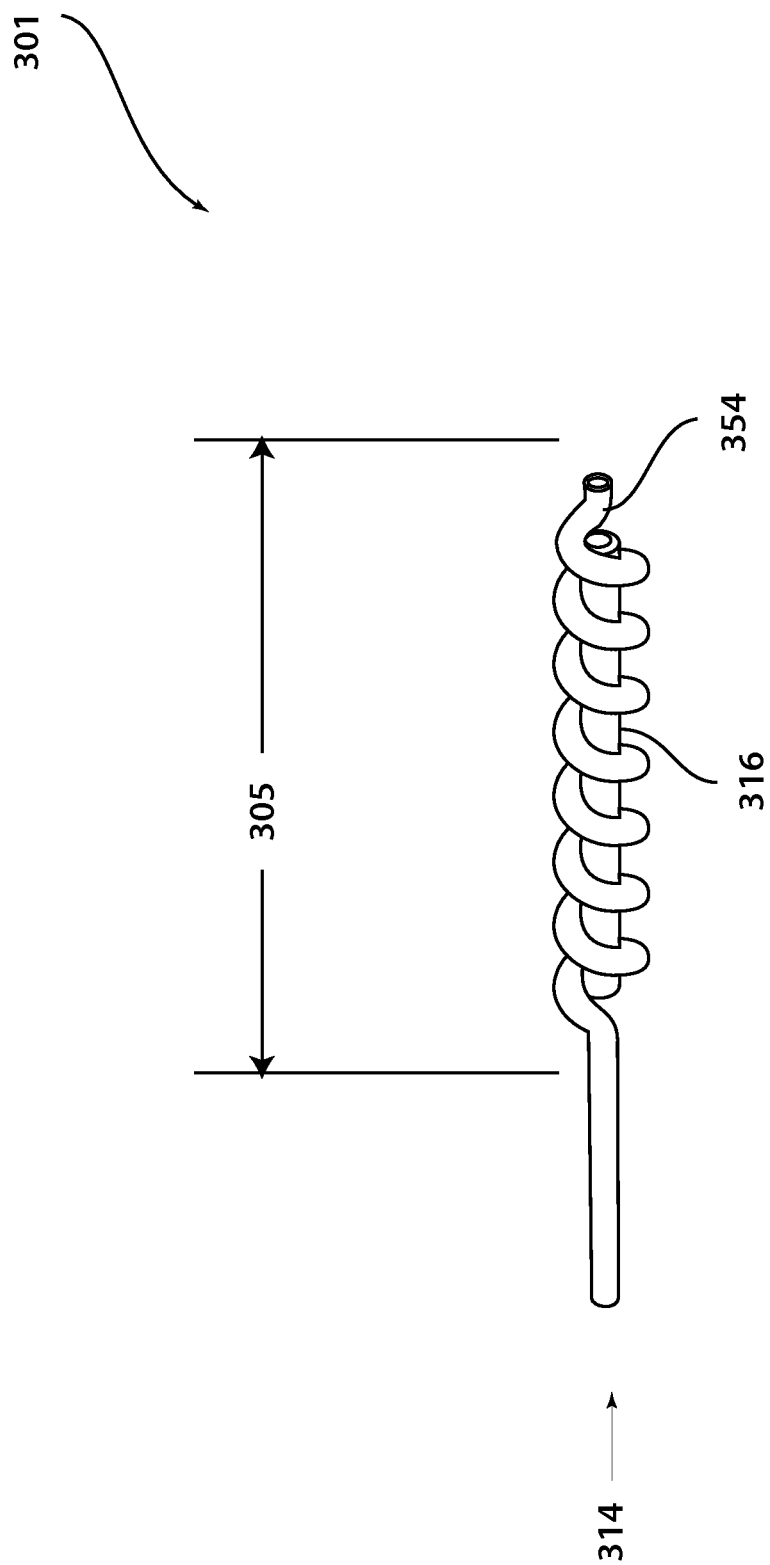
FIG. 3 is a view of a non-limiting example of a heat exchanger consistent with an exemplary embodiment of the present invention.

FIG. 3 shows another non-limiting example of a heat exchanger consistent with an exemplary embodiment of the present invention. As shown, the heat exchanger 301 has a single tube 354 that spirals (i.e., wraps) around a core 316. The single tube 354 preferably wraps around the core 316 with a consistent spiral pitch and does so in the cooling zone 305 of a cryosurgical device. The heat exchanger 301 does not include any type of diffuser. Instead, cryogen enters via an inlet flow 314 that is directed to the tube 354.

It is to be appreciated that the coiled tubes 354 may spiral at varied spiral pitches.

Figure 4A:
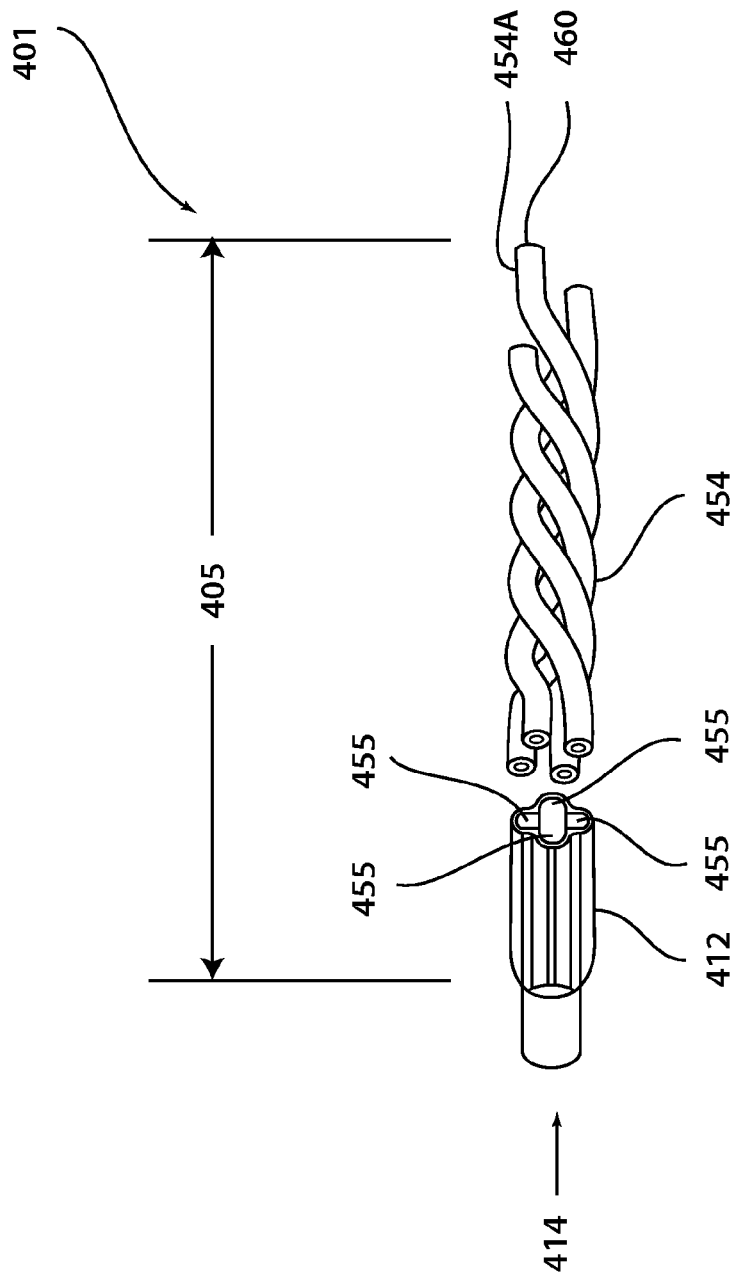
FIGS. 4A and 4B are views of non-limiting example of a heat exchanger consistent with an exemplary embodiment of the present invention.

FIG. 4A shows a non-limiting example of a heat exchanger consistent with an exemplary embodiment of the present invention. The illustrated heat exchanger 401 is similar to the heat exchanger 201 of FIG. 2 in some respects and is usable with the cryosurgical instrument 100 of FIG. 1A. As shown, the heat exchanger 401 comprises a plurality of tubes 454 that spiral in the cooling zone 405 of a cryosurgical instrument. The heat exchanger 401 differs from the heat exchanger 201 of FIG. 2 in that at least one tube 454 is longer than at least one other tube 454. For the purpose of illustration, a longer tube 454 is designated by 454A. The distal end 460 of this longer tube 454A is disposed more closely to a tip of a cryosurgical instrument (not shown) such as tip 109 of FIG. 1, such that discharge of cryogen from distal end 460 occurs more closely to tip 109, as compared to discharge from the remaining tubes 454.

Figure 4B:
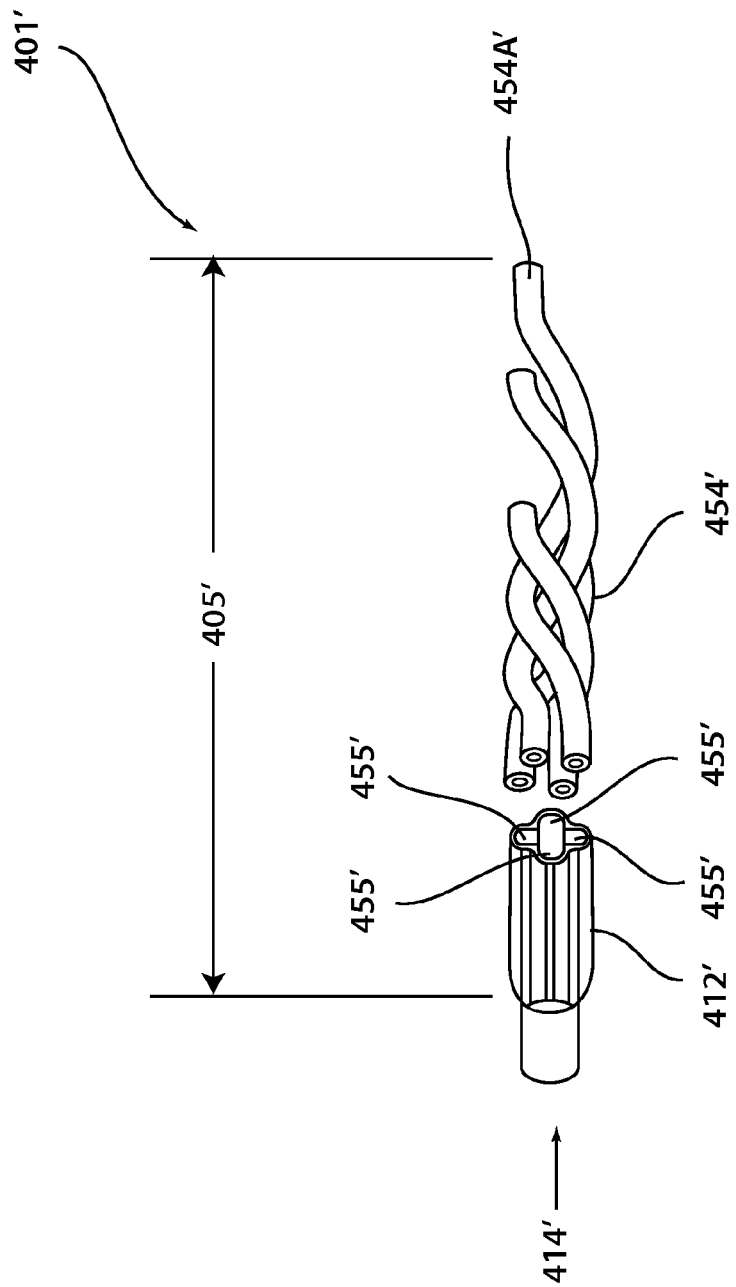

FIG. 4B shows a non-limiting example of a heat exchanger consistent with an exemplary embodiment of the present invention. The illustrated heat exchanger 401' is similar to the heat exchanger 401 of FIG. 4A in some respects. As shown, a heat exchanger 401' comprises a plurality of tubes 454'. However, in heat exchanger 401', each tube 454' is of a different length, such that discharge of cryogen from tubes 454' occurs at different points, spread along the ablation zone 405'.

It is to be appreciated that the number of coiled tubes and branches need not be four and that other numbers are both possible and contemplated. It is also to be appreciated that the coiled tubes 454 and 454' may spiral at varied spiral pitches.

Figure 5:
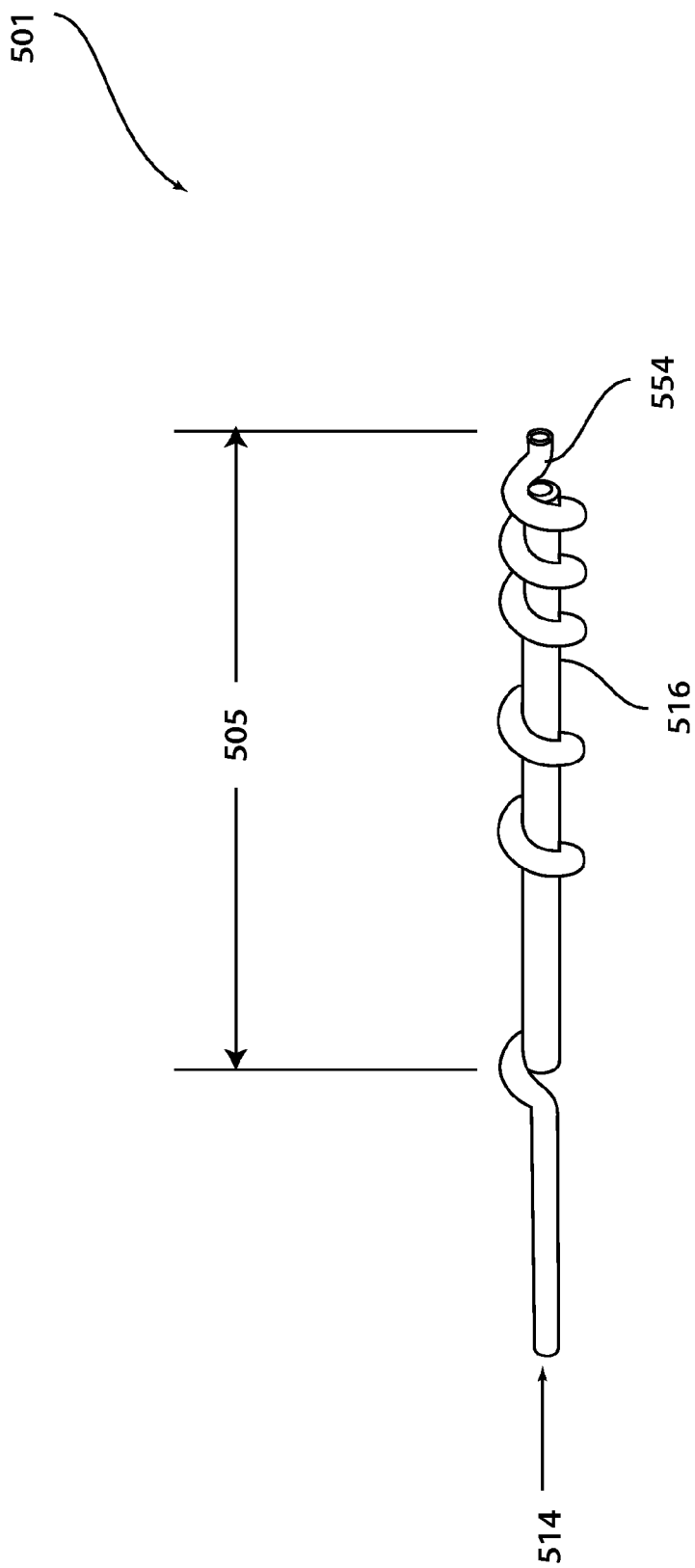
FIGS. 5 and 6 are views of non-limiting examples of heat exchangers consistent with exemplary embodiments of the present invention.

FIG. 5 shows a non-limiting example of a heat exchanger consistent with an exemplary embodiment of the present invention. The illustrated heat exchanger 501 is similar to the heat exchanger 301 of FIG. 3 in some respects. As shown, the heat exchanger 501 has a single tube 554 that spirals (wraps) around a core 516 in the cooling zone 505 of a cryosurgical instrument. Unlike the heat exchanger 301, the single tube 554 spirals around the core 516 with a varied spiral pitch. Varying the pitch of the single tube 554 alters the centrifugal forces on the cryogen at a plurality of different points along the single tube 554.

Heat exchanger 501 does not include any type of diffuser. Instead, cryogen enters via an inlet flow 514 that is directed to tube 554.

Figure 6:
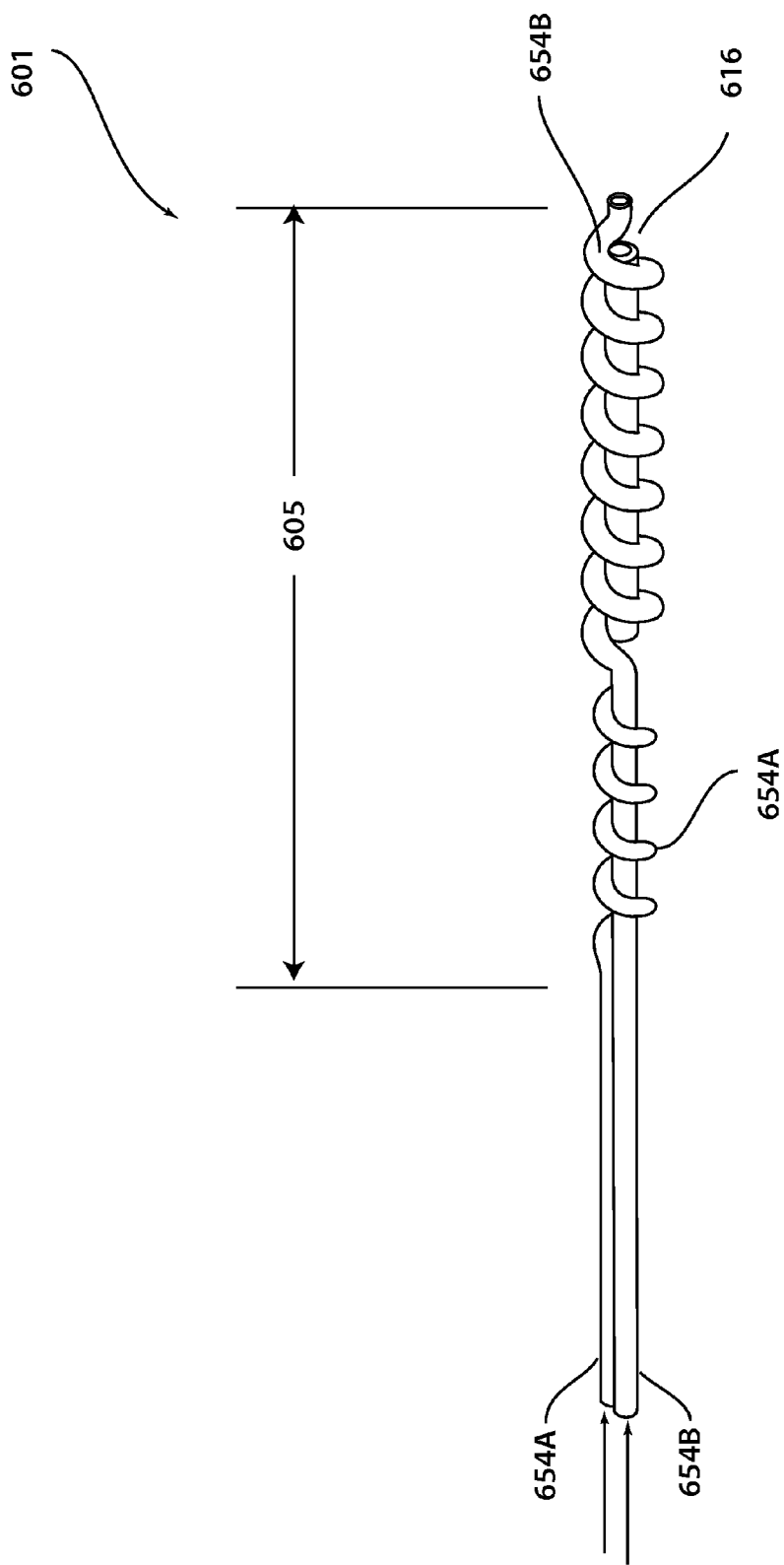

FIG. 6 shows a non-limiting example of a heat exchanger consistent with an exemplary embodiment of the present invention. The illustrated heat exchanger 601 comprises two tubes 654A and 654B. Both tubes spiral around a longitudinal axis of and in the ablation zone 605 of the heat exchanger 601. Tube 654B includes a straight (uncoiled) portion that is upstream and a spiral portion downstream that spirals (wraps) around a solid core 616 in the cooling zone 605 of a cryosurgical instrument. Tube 654A spirals (wraps around) the straight portion of tube 654B. Tubes 654A and 654B have different spiral pitches. Tubes 654A and 654B have different inlet flows of cryogen, indicated with arrows.

Heat exchanger 601 does not include any type of diffuser; instead, cryogen enters via inlet flows that are respectively directed to tubes 654A and 654B.

By way of non-limiting examples, among the many advantages of this arrangement, the inlet flow of a cryogen (whether as a liquid or as two phase (gas/liquid) flow) is subjected to a centrifugal force of rotation. Such force causes the cryogenic liquid to boil close to the outer surface of the coiled tube (for example, tubes 654A and 654B of FIG. 6), which in turn is the portion of the coiled tube that is located proximal to the inner wall of the ablation (heat exchange) zone 601. Thus, boiling occurs within the cryosurgical instrument 600 at a location that provides the most efficient heat transfer to the heat exchange zone 601, which is the desired portion of the cryosurgical instrument 600 to receive such heat transfer.

Such advantages are more apparent in case of two-phase flow since the conduction coefficient of the liquid phase to the outer surface is by far greater than the conduction coefficient of the gaseous phase, and the centrifugal forces, due to the difference in mass density. This approach is optionally and preferably used twice, in the inlet flow as well as the outlet flow, such that two coiled tubes 654A and 654B are entwined but preferably do not come into contact. Heat exchange between the inlet and the outlet flow is negligible in this arrangement, due to the small or non-existence of dT (temperature differential) to permit it.

Examples of various features/aspects/components/operations have been provided to facilitate understanding of the disclosed embodiments of the present invention. In addition, various preferences have been discussed to facilitate understanding of the disclosed embodiments of the present invention. It is to be understood that all examples and preferences disclosed herein are intended to be non-limiting.

Although selected embodiments of the present invention have been shown and described individually, it is to be understood that at least aspects of the described embodiments may be combined.

Although selected embodiments of the present invention have been shown and described, it is to be understood the present invention is not limited to the described embodiments. Instead, it is to be appreciated that changes may be made to these embodiments without departing from the principles and spirit of the invention, the scope of which is defined by the claims and the equivalents thereof.

What is claimed is:

1. A cryosurgical instrument comprising:
   a shaft having a closed distal end defining an expansion chamber and an open proximal end adapted and configured to receive an inflow of cryogen and to exhaust a flow of expanded cryogen; and
   a heat exchanger comprising:
      a solid core element extending along a longitudinal axis of the heat exchanger; and
      first and second cryogen delivery tubes, the first cryogen delivery tube including an uncoiled portion extending along the longitudinal axis and a coiled portion that spirals around and contacts the solid core element, the second cryogen delivery tube having a coiled portion that spirals around and contacts the uncoiled portion of the first cryogen delivery tube,
   wherein the coiled portions are spaced apart, and
   wherein the spirals of the cryogen delivery tubes are spaced from each other and in fluid tight contact with an inner surface of the shaft so as to form a spiraling cryogen exhaust pathway from the distal end of the shaft to the proximal end of the shaft.

2. The cryosurgical instrument of claim 1, wherein the cryogen delivery tubes have different spiral pitches.

3. The cryosurgical instrument of claim 1, wherein the cryogen delivery tubes spiral only in the ablation zone.

4. The cryosurgical instrument of claim 1, wherein the cryogen delivery tubes have a varying spiraling pitch.

* * * * *